United States Patent [19]
Petrillo, Jr. et al.

[11] 4,296,033
[45] Oct. 20, 1981

[54] 4-AZIDO-1-MERCAPTOACYL PROLINE

[75] Inventors: Edward W. Petrillo, Jr., Pennington; Frank L. Weisenborn, Titusville, both of N.J.

[73] Assignee: E. R. Squibb & Sons, Inc., Princeton, N.J.

[21] Appl. No.: 171,565

[22] Filed: Jul. 23, 1980

[51] Int. Cl.³ .................. A61K 31/40; A61K 31/445; C07D 207/16; C07D 211/34

[52] U.S. Cl. .......................... 260/326.2; 260/326.43; 260/326.47; 546/223; 546/244; 424/241; 424/246; 424/267; 424/274

[58] Field of Search ............ 260/326.2, 326.43, 326.47

[56] References Cited

U.S. PATENT DOCUMENTS

| | | | |
|---|---|---|---|
| 4,105,776 | 8/1978 | Ondetti et al. ................. | 260/326.2 |
| 4,154,935 | 5/1979 | Ondetti et al. ................. | 260/326.2 |

*Primary Examiner*—Alton D. Rollins
*Attorney, Agent, or Firm*—Lawrence S. Levinson; Donald J. Barrack

[57] ABSTRACT

1-Mercaptoacyl proline having an azido group in the 4-position inhibits the conversion of angiotensin I to angiotensin II in mammals and is useful for the treatment of hypertension.

8 Claims, No Drawings

4-AZIDO-1-MERCAPTOACYL PROLINE

RELATED APPLICATION

U.S. patent application Ser. No. 162,341, filed June 23, 1980, by Krapcho and Wade discloses 4-imido, amido and amino derivatives of 1-mercaptoacyl proline and pipecolic acid.

BACKGROUND OF THE INVENTION

The recent literature discloses a variety of mercaptoacyl amino acids which are useful for inhibiting the conversion of angiotensin I to angiotensin II in mammals, and are, therefore, useful in the treatment of hypertension.

U.S. Pat. No. 4,105,776, issued Aug. 8, 1978 discloses mercaptoacyl amino acids wherein the amino acid is, inter alia, proline, 4-hydroxyproline and 4-alkylproline.

U.S. Pat. No. 4,154,935, issued May 15, 1979 discloses mercaptoacyl amino acids wherein the amino acid is, inter alia, 4-halogen substituted proline, or 4,4-dihalogen substituted proline.

BRIEF DESCRIPTION OF THE INVENTION

Compounds having the formula

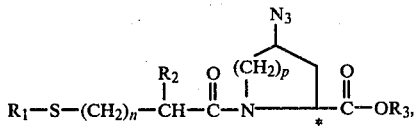

and salts thereof, inhibit the action of angiotensin converting enzyme, and are, therefore, useful for the treatment of hypertension. In formula I, and throughout the specification, the symbols are as defined below.

$R_1$ is hydrogen, alkyl, aryl, arylalkyl or a hydrolyzable acyl protecting group such as alkanoyl or arylcarbonyl;

$R_2$ is hydrogen, alkyl, alkylthio or trifluoromethyl;

$R_3$ is hydrogen, alkyl or arylalkyl;

n is 1 or 2; and p is 1 or 2.

The term "aryl," as used throughout the specification either by itself or as part of a larger group, refers to phenyl or phenyl substituted with halogen, alkyl, alkoxy, alkylthio, hydroxy, alkanoyl, nitro, amino, dialkylamino, phenyl or trifluoromethyl groups. Phenyl and monosubstituted phenyl are the preferred aryl groups; phenyl is the most preferred group.

The term "alkyl," as used throughout the specification either by itself or as part of a larger group, refers to groups having 1 to 8 carbon atoms. Alkyl groups having 1 to 3 carbon atoms are preferred.

The term "alkoxy," as used throughout the specification either by itself or as part of a larger group, refers to groups having 1 to 8 carbon atoms. Alkoxy groups having 1 to 3 carbon atoms are preferred.

The term "halogen," as used throughout the specification either by itself or as part of a larger group, refers to fluorine, chlorine, bromine and iodine. The preferred halogen groups are fluorine and chlorine.

The term "alkanoyl," as used throughout the specification either by itself or as part of a larger group, refers to groups having 1 to 9 carbon atoms.

The asterisk in formula I indicates a center of asymmetry in the ring. In the instance wherein the ring is proline (p is 1) this asymmetric center is in the L-configuration. In the instance wherein the ring is pipecolic acid (p is 2) this asymmetric center is in the D,L or L-configuration.

The carbon atom to which the azido is attached is another asymmetric center. Depending on the definition of $R_2$, the sulfur containing sidechain may also contain an asymmetric center. The product of formula I, therefore, exists in stereoisomeric forms and as racemic or diastereomeric mixtures thereof. All are within the scope of this invention. The synthesis described below can utilize the racemate or one of the enantiomers as starting materials. When the racemic starting material is used, the stereoisomers obtained in the final product can be separated by conventional chromatographic or fractional crystallization methods. Preferably, if there is an asymmetric center in the sulfur containing side-chain, it is in the D-configuration.

DETAILED DESCRIPTION OF THE INVENTION

The compounds of formula I, and salts thereof, are useful as hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., humans. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one or a combination of the compounds of this invention, angiotensin dependent hypertension in the species of mammal (e.g., humans) suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 300 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methychlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration or in sterile solutions or suspensions for parenteral administration. About 10 to 500 mg. of a compound or mixture or compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of this invention can be prepared using as starting materials compounds having the formula

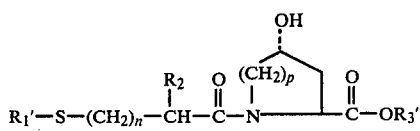

wherein $R_1'$ is alkyl, aryl, arylalkyl or a hydrolyzable acyl protecting group and $R_3'$ is alkyl or arylalkyl. Methodology for preparing the compounds of formula II is described in the patent literature; see, for example, U.S. Pat. No. 4,105,776, issued Aug. 8, 1978. As described therein, compounds of formula II can be prepared by acylation of an amino acid having the formula

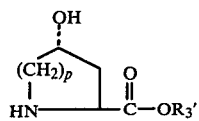

(or an acid addition salt thereof) with a carboxylic acid having the formula

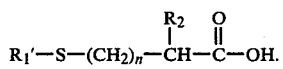

The acylation reaction can be run in the presence of a coupling agent such as dicyclohexylcarbodiimide, or the acid can be activated by formation of its mixed anhydride, symmetrical anhydride, acid halide (preferably acid chloride) or acid ester, or by the use of Woodward reagent K, N-ethoxycarbonyl-2-ethoxy-1,2-dihydroquinoline or the like. For a review of these methods of acylation reference can be made to *Methoden der Organischen Chemie* (Houben-Weyl), Vol. XV, part II, page 1 et seq (1974).

Reaction of a compound of formula II with hydrazoic acid in the presence of diethylazodicarboxylate and triphenylphosphine yields the corresponding product having the formula

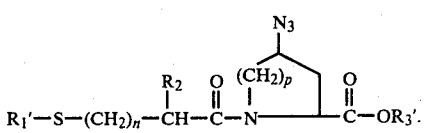

Those products of formula I wherein one, or both, of $R_1$ and $R_3$ is hydrogen can be prepared from products of formula V. To prepare a product of formula I wherein $R_1$ and $R_3$ are both hydrogen, i.e., a product having the formula

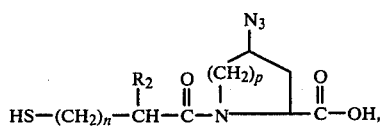

a product of formula V wherein $R_1'$ is a hydrolyzable acyl protecting group can be hydrolyzed in an inert atmosphere. Those products of formula I wherein $R_1$ is hydrogen and $R_3$ is other than hydrogen can be prepared by esterification of the corresponding compound of formula VI with an alcohol ($R_3'$—OH) using dicyclohexylcarbodiimide and dimethylamino pyridine, or an acid catalyst such as sulfuric acid or by reaction with the appropriate diazo compound. Those products of formula I wherein $R_3$ is hydrogen and $R_1$ is alkyl, aryl or arylalkyl can be prepared by reacting the corresponding compound of formula VI with the appropriate alkyl, aryl, or arylalkyl halide in the presence of a base such as ammonia, pyridine, sodium methoxide or the like. Those compounds of formula I wherein $R_3$ is hydrogen and $R_1$ is a hydrolyzable acyl protecting group can be prepared by acylation of the corresponding compound of formula VI with the appropriate acid halide, or using one of the acylation methods described above.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic physiologically acceptable salts are preferred, although other salts are also useful, e.g., in isolating or purifying the product.

The salts are formed in a conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired another salt formed.

Those products of formula I wherein n is 1, p is 1, and $R_2$ is methyl or trifluoromethyl are preferred. Also preferred are those compounds of formula I wherein $R_3$ is hydrogen.

The following examples are specific embodiments of this invention.

EXAMPLE 1

[1(S),4S]-4-Azido-1-[3-(benzoylthio)-2-methyl-1-oxopropyl]-L-proline, methyl ester (A)

[1(S),4R]-1-[3-(benzoylthio)-2-methyl-1-oxopropyl]-4-hydroxyl-L-proline, methyl ester trans-4-Hydroxy-L-proline, methyl ester (0.02 mole) is dissolved in 75 ml of dichloromethane and cooled to 5° C. in an ice-bath under argon. 3-(Benzoylthio)-2-methylpropanoic acid (4.49 g, 0.02 mole) and N,N'-dicyclohexylcarbodiimide (4.13 g, 0.02 mole) in 25 ml of dichloromethane are then added. After 0.5 hours the ice-bath is removed and the reaction is allowed to warm to room temperature and stir for about 16 hours. The mixture is filtered and the filtrate concentrated in vacuo yielding an oily residue. The residue is taken up in ether (30 ml) and filtered to remove additional solid, redissolved in 125 ml of dichloromethane and washed with 50 ml each of 5% KHSO$_4$, saturated NaHCO$_3$, brine, and dried (MgSO$_4$). The residue after evaporation is preabsorbed on 120 ml of silica gel and the material chromatographed on silica gel (1000 ml), eluting with ethyl acetate, methylene chloride (1:4) to give 6.1 g of the title compound.

(B)

[1(S),4S]-4-Azido-1-]3-(benzoylthio)-2-methyl-1-oxopropyl]-L-proline, methyl ester Diethylazodicarboxylate (1.04 g, 0.006 mole) in acetonitrile (5 ml) is added to a mixture of [1(S),4R]-1-]3-(benzoylthio)-2-methyl-1-oxopropyl]-L-proline, methyl ester (1.05 g, 0.003 mole), triphenylphosphine (1.58 g, 0.006 mole) and 12.5 ml of 5.4% hydrazoic acid in benzene (0.015 mole, 5 equivalents) in 40 ml of dry acetonitrile over 0.5 hour with stirring. After 6 hours, thin layer chromatography (tlc) shows the starting proline derivative to be still present, so additional triphenylphosphine (0.40 g, 0.0015 mole) diethylazodicarboxylate (0.26 g, 0.0015 mole) and hydrazoic acid solution in benzene (4.0 ml, 0.0075 mole) are added and the mixture is allowed to stir for 6 hours. The solvents are removed by evaporation in vacuo yielding a semi-solid residue. Trituration with ether and filtration removes most of the solid. The crude product is preadsorbed on 25 ml of silica gel and the material is then flash chromatographed on silica gel (250 ml), eluting with ether:hexane (1:1) to yield 0.71 g of pure product as an oil (tlc R$_f$=0.48, ether). IR shows absence of hydroxy group (3310 cm$^{-1}$) and presence of azide (2120 cm$^{-1}$).

EXAMPLE 2

[1(S),4S]-4-Azido-1-(3-mercapto-2-methyl-1-oxopropyl)-L-proline

[1(S),4S]-4-Azido-1-]3-(benzoylthio)-2-methyl-1-oxopropyl]-L-proline, methyl ester (1.0 g, 0.00266 mole) is dissolved in 25 ml of absolute methanol and the mixture is purged three times with argon. Sodium hydroxide (5.5 ml, 1.0 N) is added under argon (total exclusion of air is necessary) and the mixture is stirred for 24 hours. The mixture is acidified with 1.0 N hydrochloric acid to pH 5 and extracted with three 30 ml portions of ethyl acetate. The extracts are combined, dried (MgSO$_4$) and evaporated yielding 0.65 g oily syrup. The crude material is preadsorbed on 25 ml of silica gel and flash chromatographed on silica gel (250 ml), eluting with benzene/acetic acid (4:1) to yield 0.468 g of the title compound as a heavy oil.

A portion of the above oil (0.100 g, 0.0039 mole) is dissolved in 10 ml of ethyl acetate and 1 equivalent of adamantene amine is added with stirring. The white precipitate is collected and washed with cold ethyl acetate to yield the adamantane amine salt of the title compound, melting point 168°-172° C.

Analysis* Calc'd for C$_{20}$H$_{33}$N$_5$SO$_{3.5}$, MW 431.57 C, 55.66; h, 7.71; N, 16.33; S, 7.43. Found: C, 55.56; H, 7.89; N, 16.49; S, 7.59; SH, 99.6%.

* (1:1) Adamantane amine salt+¼ mole of ethyl acetate

EXAMPLES 3–7

Following the procedure of Example 1, but substituting the compound listed in column I for trans-4-hydroxy-L-proline methyl ester and the compound listed in column II for 3-(benzoylthio)-2-methylpropanoic acid, yields the compound listed in column III.

|    | Column I | Column II | Column III |
|----|----------|-----------|------------|
| 3. | trans-4-hydroxy-pipecolic acid, methyl ester | 3-(acetylthio)-2-methylpropanoic acid | [1(S),4S]-1-[3-(acetylthio)-2-methyl-1-oxopropyl]-4-azidopipecolic acid, methyl ester |
| 4. | trans-4-hydroxy-L-proline, methyl ester | 3-(acetylthio)-2-(trifluoromethyl)propanoic acid | [1(S),4S]-1-[3-(acetylthio)-1-oxo-2-(trifluoromethyl)propyl]-4-azido-L-proline, methyl ester |
| 5. | trans-4-hydroxy-L-pipecolic acid, benzyl ester | 3-(acetylthio)-2-(methylthio)propanoic acid | [1(S),4S]-1-[3-(acetylthio)-2-methylthio)-1-oxopropyl]-4-azido-L-pipecolic acid, benzyl ester |
| 6. | trans-4-hydroxy-L-proline, benzyl ester | 3-(benzoylthio)propanoic acid | [1(S),4S]-4-azido-1-3[3-benzoylthio)-1-oxopropyl]-L-proline, benzyl ester |
| 7. | trans-4-hydroxy-L-proline, methyl ester | 4-(acetylthio)butyric acid | [1(S),4S]-1-[4-(acetylthio)-1-oxobutyl]-4-azido-L-proline, methyl ester |

What is claimed is:

1. A compound having the formula

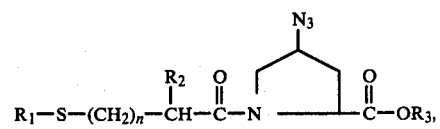

or a salt thereof, wherein,

R$_1$ is hydrogen, alkyl, aryl, arylalkyl, alkanoyl, or arylcarbonyl;

R$_2$ is hydrogen, alkyl, alkylthio or trifluoromethyl;

R$_3$ is hydrogen, alkyl or arylalkyl; and n is 1 or 2;

wherein the asymmetric center indicated by the asterisk (*) is in the L-configuration and wherein the term "aryl" refers to phenyl or phenyl substituted with halogen, alkyl, alkoxy, alkylthio, hydroxy, alkanoyl, nitro, amino, dialkylamino, phenyl or trifluoromethyl groups.

2. A compound in accordance with claim 1 wherein $R_1$ and $R_3$ are hydrogen.

3. A compound in accordance with claim 1 wherein $R_2$ is methyl or trifluoromethyl.

4. A compound in accordance with claim 3 wherein $R_2$ is methyl.

5. A compound in accordance with claim 1 wherein n is 1.

6. A compound in accordance with claim 1 wherein n is 1 and $R_2$ is methyl.

7. The compound in accordance with claim 1 [1(S),4S]-4-azido-1-]3-(benzoylthio)-2-methyl-1-oxo-propyl]-L-proline, methyl ester.

8. The compound in accordance with claim 1 [1(S),4S]-4-azido-1-(3-mercapto-2-methyl-1-oxo-propyl)-L-proline.

* * * * *

UNITED STATES PATENT AND TRADEMARK OFFICE
CERTIFICATE OF CORRECTION

PATENT NO. : 4,296,033

DATED : October 20, 1981

INVENTOR(S) : Edward W. Petrillo, et al

It is certified that error appears in the above—identified patent and that said Letters Patent is hereby corrected as shown below:

In column 5, line 19, please delete "]" before "3" and add in its place --[--.

In column 5, line 65, please delete "]" before "3" and add in its place --[--.

In column 6, line 18, "h, 7.71" should read --H, 7.71--.

In the table, columns 5 and 6, example 5, column III, second line of the example, add "(" before methylthio.

In the table, columns 5 and 6, example 6, column III, first line of the example, delete "3" first occurrence.

UNITED STATES PATENT AND TRADEMARK OFFICE
CERTIFICATE OF CORRECTION

PATENT NO. : 4,296,033

DATED : December 11, 1981

INVENTOR(S) : Edward W. Petrillo, et al

It is certified that error appears in the above—identified patent and that said Letters Patent is hereby corrected as shown below:

In column 6, the structural formula in claim 1 should read:

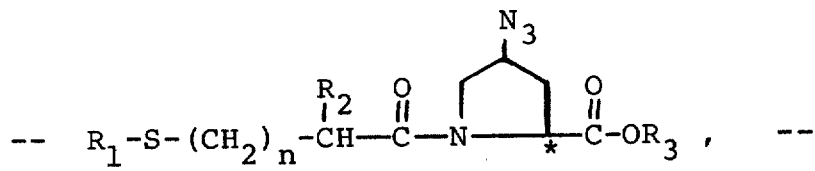

In column 8, line 4, please delete "]" before "3" and add in its place --[--.

Signed and Sealed this

Ninth Day of February 1982

|SEAL|

Attest:

GERALD J. MOSSINGHOFF

Attesting Officer    Commissioner of Patents and Trademarks